US00PP22509P2

(12) United States Plant Patent
Verschoor

(10) Patent No.: US PP22,509 P2
(45) Date of Patent: Feb. 21, 2012

(54) *VERONICA* PLANT NAMED 'BLUE BOMB'

(50) Latin Name: ***Veronica* sp.**
Varietal Denomination: Blue Bomb

(76) Inventor: Jan Verschoor, Haarlem (NL)

( * ) Notice: Subject to any disclaimer, the term of this patent is extended or adjusted under 35 U.S.C. 154(b) by 0 days.

(21) Appl. No.: 12/931,484

(22) Filed: Feb. 2, 2011

(51) Int. Cl.
*A01H 5/00* (2006.01)

(52) U.S. Cl. ..... Plt./251

(58) Field of Classification Search ..... Plt./251
See application file for complete search history.

*Primary Examiner* — Kent L Bell

(74) *Attorney, Agent, or Firm* — Jondle & Associates, P.C.

(57) ABSTRACT

A *Veronica* plant particularly distinguished by a compact, well-branched plant habit, strong stems, strongly-branched, compact inflorescences, a very floriferous blooming habit with re-blooming and easy to grow a strong and well-developed plant in one season, is disclosed.

2 Drawing Sheets

Genus and species; *Veronica* sp.
Variety denomination: 'Blue Bomb'.

BACKGROUND OF THE NEW PLANT

The present invention comprises a new and distinct variety of *Veronica*, botanically known as *Veronica* sp., and hereinafter referred to by the variety name 'Blue Bomb'. 'Blue Bomb' was developed through a cross conducted in the summer of 2006 between the female, an un-named proprietary *Veronica* sp. seedling (unpatented) and the male parent, an un-named proprietary *Veronica* sp. seedling (unpatented) in Haarlem, The Netherlands. 'Blue Bomb' was selected as a single plant in June 2007 and was first propagated in summer 2007 via softwood cuttings in Haarlem, The Netherlands.

'Blue Bomb' has been propagated for approximately 4 generations via softwood cuttings and has been found to retain its distinctive characteristics through successive asexual propagations via softwood cuttings.

Plant Breeder's Rights for this variety have not been applied for. 'Blue Bomb' has not been made publicly available or sold more than one year prior to the filing date of this application.

SUMMARY OF THE INVENTION

The following are the most outstanding and distinguishing characteristics of this new cultivar when grown under normal horticultural practices in Haarlem, The Netherlands.

1. A compact, well-branched plant habit;
2. Strong stems;
3. Strongly-branched, compact inflorescences;
4. A very floriferous blooming habit with re-blooming; and
5. Easy to grow a strong and well-developed plant in one season.

DESCRIPTION OF THE PHOTOGRAPHS

This new *Veronica* plant is illustrated by the accompanying photographs which show blooms, buds, and foliage of the plant in full color; the colors shown are as true as can be reasonably obtained by conventional photographic procedures. The photographs are of two-year-old plants grown in Haarlem, The Netherlands in July 2010.

DESCRIPTION OF THE NEW CULTIVAR

Figure 1:
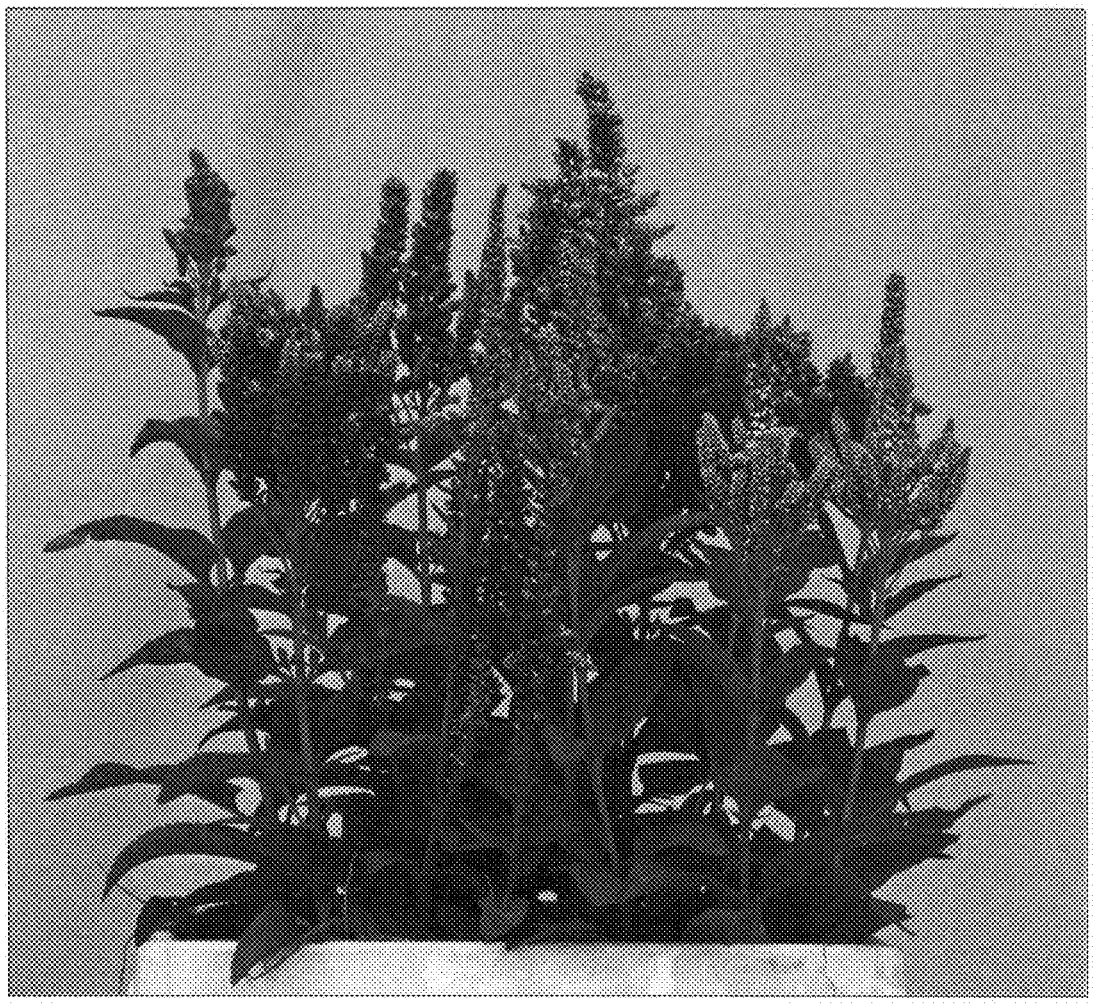
FIG. 1 shows a whole plant, including leaves, buds and inflorescence.
Figure 2:
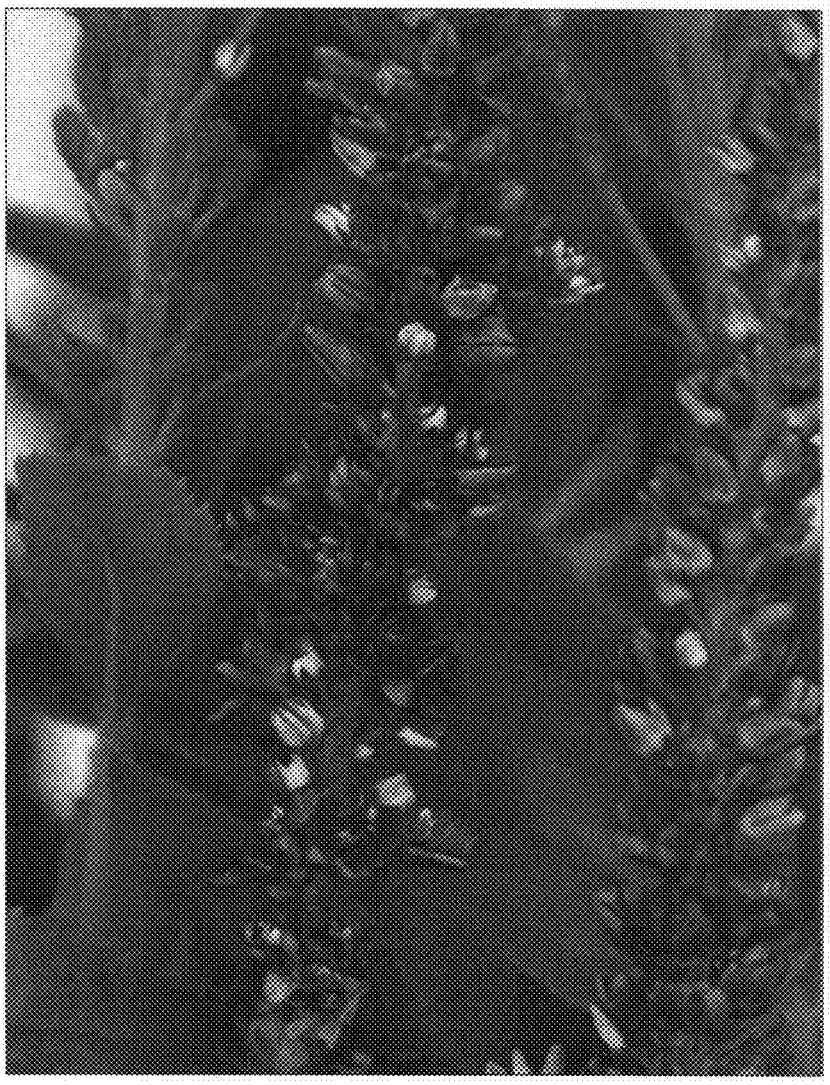
FIG. 2 shows a close-up of the inflorescence.
Figure 3:
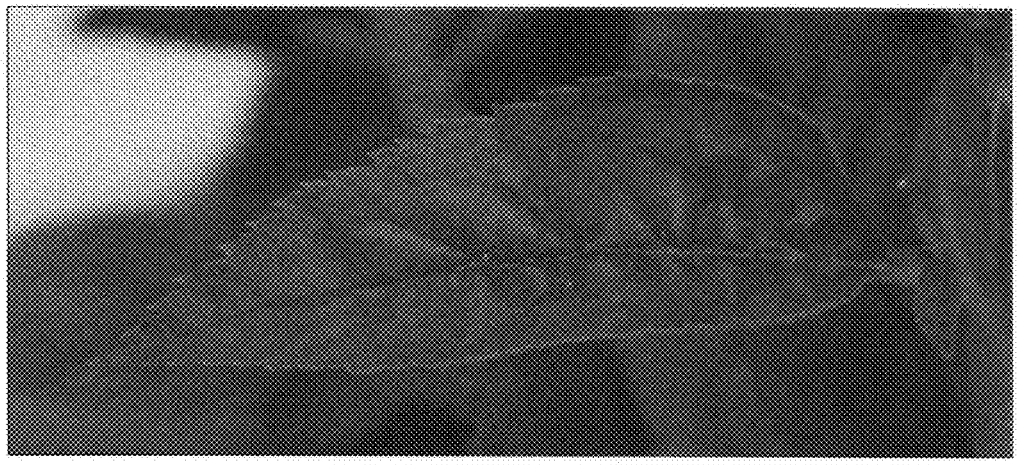
FIG. 3 shows a close-up of a mature leaf.

The following detailed descriptions set forth the distinctive characteristics of 'Blue Bomb'. The data which define these characteristics were collected from asexual reproductions carried out in Haarlem, The Netherlands. The plant history was taken on two-year-old plants grown outdoors in Haarlem, The Netherlands in July 2010. Color readings were taken under natural light. Color references are primarily to The R.H.S. Colour Chart of The Royal Horticultural Society of London (R.H.S.) (2007 edition).

DETAILED BOTANICAL DESCRIPTION OF THE NEW PLANT

Classification:
- *Family.*—Scrophulariaceae.
- *Botanical name.*—*Veronica* sp.
- *Denomination.*—'Blue Bomb'.

Parentage:
- *Female parent.*—An un-named, proprietary *Veronica* sp. seedling (unpatented).
- *Male parent.*—An un-named, proprietary *Veronica* sp. seedling (unpatented).

Growth:
- *Plant habit.*—Broad upright.
- *Life cycle.*—Herbaceous Perennial.
- *Shape.*—Broad inverted triangle.
- *Growth rate.*—In the spring, about 8.0 cm per month.
- *Vigor.*—Low to moderate.
- *Plant height* (*from top of soil*).—34.4 cm.
- *Plant width* (*horizontal plant diameter*).—31.9 cm.
- *Time to produce a finished flowering plant.*—About 4 months.
- *Branching description.*—Freely branching from the base.
- *Basal branching.*—Yes.

*Average number of lateral branches per plant.*—About 15.

*Lateral branch length* (*excluding the inflorescence*).—20.1 cm.

*Lateral branch diameter.*—3.0 mm.

*Internode length.*—3.6 cm.

*Root description.*—Dense, low-branching, thin, fleshy and long.

*High temperature tolerance.*—At least tolerant to temperatures up to 35 degrees Celsius.

*Low temperature tolerance.*—At least tolerant to temperatures as low as USDA Zone 4.

Stem:

*Appearance.*—Rounded and slightly glossy.

*Aspect.*—Rounded.

*Strength.*—Strong.

*Color.*—RHS 143B and RHS 143C (Green).

*Pubescence.*—Densely pubescent; average length of hairs is 0.2 mm and greenish-white (the pubescence is too small to be accurately measured by RHS).

Leaves:

*Durability of foliage to stress.*—High.

*Arrangement and type.*—Opposite, single.

*Quantity of leaves per lateral branch.*—12 (6 pairs).

*Shape.*—Narrow ovate.

*Apex.*—Acute.

*Base.*—Truncate.

*Margin.*—Serrate (4.5 teeth per cm).

*Length.*—6.7 cm.

*Width.*—2.9 cm.

*Texture.*—Moderately glossy; upper surface is smooth and lower surface is sparsely pubescent with very short hairs that are 0.3 mm in length, and greenish-white (hairs are too small to be accurately measured with RHS).

*Venation pattern.*—Pinnate.

*Venation color.*—Upper surface: RHS 144A (Yellow-green). Lower surface: RHS 143C (Green).

*Immature leaf color.*—Upper surface: RHS 143A (Green). Lower surface: RHS 146B (Yellow-green).

*Mature leaf color.*—Upper surface: RHS N137B (Green) to RHS 147A (Yellow-green). Lower surface: RHS 147B (Yellow-green).

*Petiole.*—Shape: V-shaped. Length: 1.1 cm. Diameter: Average width is 2.5 mm. Color: RHS 143B.

Inflorescence:

*Arrangement.*—Compound terminal raceme.

*Height.*—11.5 cm.

*Width.*—6.9 cm.

*Quantity of flowers per inflorescence.*—Primary racemes average about 100; secondary racemes average about 75; each inflorescence holds an average of 16 secondary racemes.

*Flowering habit* (*length of flowering season*).—Continuously from July to late September.

*Quantity of flowers per lateral stem.*—650.

*Quantity of flower buds per lateral stem.*—650.

*Quantity of flowers and buds per plant.*—20,000.

*Time to flower.*—Approximately 8 months when field-grown.

*Fragrance.*—Faint, sweet.

*Rate of flower opening.*—Approximately 20% are open at any given time.

Flower buds:

*Length.*—4.5 mm.

*Diameter.*—2.5 mm.

*Shape.*—Ovate.

*Rate of opening.*—Approximately 20% opens at once; all flowers have opened in approximately 8 weeks.

*Color.*—RHS 93C (Violet-blue) and tip is slightly tinged with RHS N81C (Purple-violet).

Flowers:

*Aspect.*—Outward.

*Type.*—Campanulate.

*Lastingness of flowers on the plant.*—Approximately 7 days.

*Diameter.*—7.0 mm.

*Depth.*—5.0 mm.

*Persistent or self-cleaning.*—Self-cleaning.

*Petals.*—Quantity per flower: 5. Arrangement: Campanulate, lower 40% fused. Shape: Oblanceolate. Apex: Broad acute. Base: Fused. Margin: Entire. Length: 5.0 mm. Width: 2.0 mm and upper petals average 2.5 mm.

*Color, when opening* (*both upper and lower surfaces*).—RHS 90B (Violet-blue).

*Color, fully opened.*—Upper surface: RHS 90D (Violet-blue). Lower surface: RHS 90C and RHS 90D (Violet-blue).

*Calyx.*—Shape: Rotate. Length: 1.5 mm. Diameter: 2.0 mm.

*Sepals.*—Arrangement: Rotate. Texture: Dull, smooth. Quantity per flower: 5. Shape: Narrow ovate. Apex: Acute. Base: Cuneate, lower 5% fused. Margin: Entire. Length: 1.5 mm. Width: 0.75 mm. Color: Immature (both surfaces): RHS 137B (Green). Mature (both surfaces): RHS 137B and RHS 137C (Green).

*Peduncle.*—Length: 10.9 cm. Diameter: 3.0 mm. Color: RHS 143B and RHS 143C (Green). Angle: Primary racemes are straight upright, secondary racemes are at an average angle of 25 degrees. Strength: Strong.

*Pedicel.*—Length: 1.5 mm. Diameter: 0.5 mm. Angle: 60 degrees. Strength: Strong. Color: RHS 143B and RHS 143C (Green).

Reproductive organs:

*Stamens.*—Number: In most flowers, no stamens are present; occasionally flowers have one deformed stamen. Filament: Color: RHS N88A and RHS N88B (Violet). Length: 2.0 mm. Anthers: Shape: Dorsifixed, elliptic. Width: 2.0 mm. Color: RHS N77B (Purple). Pollen amount: Absent.

*Pistils.*—Number: 1. Pistil length: 3.0 mm. Stigma: Color: RHS N92A (Violet-blue). Shape: Clavate. Style: Color: RHS 86A (Violet). Length: 2.5 mm.

*Ovary.*—Color: RHS 144B (Yellow-green).

Fruit/seed set: No fruit or seeds observed

Disease and insect resistance: No more susceptible or resistant than other *Veronica* varieties.

COMPARISON WITH PARENTAL AND COMMERCIAL VARIETY

'Blue Bomb' differs from the female parent, a proprietary un-named *Veronica* plant (unpatented) in that 'Blue Bomb' has more strongly branched and compact inflorescences and a darker blue inflorescence color than the female parent.

The male parent of 'Blue Bomb' is no longer available for comparison.

'Blue Bomb' differs from the commercial variety 'Sunny Border Blue' (unpatented) in that 'Blue Bomb' has a compact, well-branched plant habit, strong stems, strongly branched inflorescences and re-blooming, while 'Sunny Border Blue' has a less compact and branched habit, weaker stems, less branched inflorescences and does not re-bloom.

I claim:

1. A new and distinct variety of *Veronica* plant as described and shown herein.

* * * * *